United States Patent
Nabatame

(10) Patent No.: US 7,372,939 B2
(45) Date of Patent: May 13, 2008

(54) X-RAY COMPUTED TOMOGRAPHIC APPARATUS

(75) Inventor: Takeo Nabatame, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 11/465,616

(22) Filed: Aug. 18, 2006

(65) Prior Publication Data

US 2007/0081624 A1     Apr. 12, 2007

(30) Foreign Application Priority Data

Aug. 25, 2005   (JP)   ............... 2005-244435

(51) Int. Cl.
    *A61B 6/03*   (2006.01)
(52) U.S. Cl. .......................... 378/19; 378/98
(58) Field of Classification Search .............. 378/4,
    378/11, 16, 98, 19
    See application file for complete search history.

(56) References Cited

U.S. PATENT DOCUMENTS

| 4,991,190 A | * | 2/1991 | Mori | ............ 378/9 |
|---|---|---|---|---|
| 5,848,117 A | * | 12/1998 | Urchuk et al. | ............ 378/19 |
| 2003/0031290 A1 | * | 2/2003 | Sugihara et al. | ............ 378/15 |
| 2003/0076920 A1 | * | 4/2003 | Shinno et al. | ............ 378/4 |
| 2006/0104407 A1 | * | 5/2006 | Zamyatin et al. | ............ 378/4 |

FOREIGN PATENT DOCUMENTS

JP          8-602          1/1996

* cited by examiner

*Primary Examiner*—Chih-Cheng G Kao
(74) *Attorney, Agent, or Firm*—Oblon, Spivak, McClelland, Maier & Neustadt, P.C.

(57) ABSTRACT

An X-ray computed tomographic apparatus includes an X-ray tube that generates X-ray, an X-ray detector that detects an X-ray passing through an object, a supporting member that rotatably supports the X-ray tube and the X-ray detector around a rotational axis, a reconstructing unit that reconstructs an image on the basis of an output of the X-ray detector, an information creating unit that creates information concerning an arrangement of an asymmetrical field of view of the object when the field of view of the scanogram by the X-ray tube and the X-ray detector is asymmetric with respect to an imaging center line in a direction perpendicular to the rotational axis, and a display unit that displays information concerning the created arrangement.

5 Claims, 17 Drawing Sheets

X-RAY COMPUTED TOMOGRAPHIC APPARATUS

CROSS-REFERENCE TO RELATED APPLICATIONS

This application is based upon and claims the benefit of priority from prior Japanese Patent Application No. 2005-244435, filed Aug. 25, 2005, the entire contents of which are incorporated herein by reference.

BACKGROUND OF THE INVENTION

1. Field of the Invention

The present invention relates to an X-ray computed tomographic apparatus having an asymmetrical X-ray detector.

2. Description of the Related Art

The asymmetrical X-ray detector includes an X-ray detector in which a detection region of X-ray that passes through an object is asymmetric with respect to an imaging center line in a channel direction. In detail, in the asymmetrical X-ray detector, the imaging center line is disposed between X-ray detecting channels, and the number of X-ray detecting channels that is positioned at one side of the imaging center line is larger than the number of X-ray detecting channels that is positioned at the other side of the imaging center line. Further, the asymmetrical X-ray detector includes a multichannel X-ray detector in which the center is shifted from a line connecting a focal point of the X-ray and a rotating center of a tube toward the channel direction.

In accordance with the asymmetrical property of the detector, an X-ray beam is formed to be an asymmetrical sectorial formed by a slit. The asymmetrical X-ray detector can have a wider field of view for imaging (hereinafter, referred to as imaging FOV) than a symmetrical X-ray detector having the same number of channels. This X-ray detector is applicable when determining a portion to be treated by raising a right arm to image.

When a reconstructing process is performed on a tomographic image, a portion whose data is lost is supplemented by a complementary data to secure a field of view of reconstructing (hereinafter, referred to as reconstructing FOV) having the same level as the imaging FOV.

When a flat transmission image such as an X-ray image is acquired by a scanogram method, the image is configured by an asymmetrical channel arrangement. Therefore, the right and left of the imaging region are not symmetric to each other. The situation where the image is partially lost is not unavoidable in the case that the object is relatively large. As a result, it is needed to set a scanogram angle the by considering the above fact.

However, since a portion in which some of the image is lost is changed in a top or bottom, left or right direction corresponding to the position of the X-ray tube, it is difficult to be able to perceive the loss of the partial image. Further, the operability is bad.

BRIEF SUMMARY OF THE INVENTION

Accordingly, it is an object of the present invention to provide an X-ray computed tomographic apparatus having an asymmetrical multichannel X-ray detector which is capable of improving an operability for setting of a scanogram angle.

According to a first aspect of this invention, an X-ray computed tomographic apparatus includes an X-ray tube that generates X-rays, an X-ray detector that detects an X-ray passing through an object, a supporting member that rotatably supports the X-ray tube and the X-ray detector around a rotational axis, a reconstructing unit that reconstructs an image on the basis of an output of the X-ray detector, an information creating unit that creates information concerning an arrangement of an asymmetrical field of view of the object when the field of view of the scanogram by the X-ray tube and the X-ray detector is asymmetric with respect to an imaging center line in a direction perpendicular to the rotational axis, and a display unit that displays information concerning the created arrangement.

According to a second aspect of this invention, an X-ray computed tomographic apparatus includes an X-ray tube that generates X-ray, an X-ray detector that has an asymmetrical property with respect to an imaging center line, a reconstructing unit that reconstructs an image on the basis of an output of the X-ray detector, and a display unit that displays a positional relationship between an object and a field of view of the scanogram using an asymmetrical sectorial picture corresponding to the asymmetrical property of the X-ray detector.

According to a third aspect of this invention, an X-ray computed tomographic apparatus includes an X-ray tube that generates X-ray, an X-ray detector that detects an X-ray passing through an object, a collimator that forms the X-ray so as to be asymmetric with respect to an imaging center line, a reconstructing unit that reconstructs an image on the basis of an output of the X-ray detector, and a display unit that displays a positional relationship between an object and a field of view of the scanogram using an asymmetrical sectorial picture corresponding to the asymmetrically formed X-ray.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 4 is a diagram showing an example of a display screen corresponding to a step S14 of FIG. 3;

FIG. 5 is a diagram showing an example of a display screen corresponding to a step S16 of FIG. 3;

FIG. 7 is a diagram showing an example of a display screen corresponding to a step S18 of FIG. 3;

FIG. 8 is a diagram showing a sub-window at a scanogram angle of 0° corresponding to a step S19 of FIG. 3;

FIG. 9 is a diagram showing a sub-window at a scanogram angle of 180° corresponding to a step S19 of FIG. 3;

FIG. 12 is a diagram showing an example of a screen display corresponding to FIG. 7 in the case of a double tube type X-ray CT apparatus;

FIG. 14 is a diagram showing an example of a screen display at scanogram angles of 180°/90° corresponding to FIG. 8 in the case of a double tube type X-ray CT apparatus;

DETAILED DESCRIPTION OF THE INVENTION

Hereinafter, embodiments of this invention will be described with reference to accompanying drawings. In order to reconstruct one slice of tomographic image data in an X-ray computed tomographic apparatus, 360° projection of the object is required so as to obtain data. Further, even when using a half scanning method, projection data corresponding 180°+ view angle is required. This invention is applicable for any type of reconstruction methods. Hereinafter, the half scanning method will be exemplified. A mechanism that converts incident X-ray into electric charges mainly includes an indirect conversion method and a direct conversion method. The indirect conversion method converts the X-ray into light using a fluorescent substance such as a scintillator and then converts the light into electric charges using a photoelectric conversion element such as a photodiode. Further, the direct conversion method uses a photoconductive effect, that is, generates an electron-hole pair in a semiconductor by the X-ray and moves into an electrode. Even though any of the methods can be used as the X-ray detecting element, the indirect conversion type will be described in this specification. In recent years, the number of a plurality of detectors has increased, and currently, 64 rows (64 segments) or more of detectors is being practically used. This invention is applicable to an X-ray computed tomographic apparatus including a multislice (refers to two dimensional array type) detector as well as a singleslice detector according to a related art. In here, an X-ray computed tomographic apparatus including a single-slice detector will be exemplified.

Figure 1:
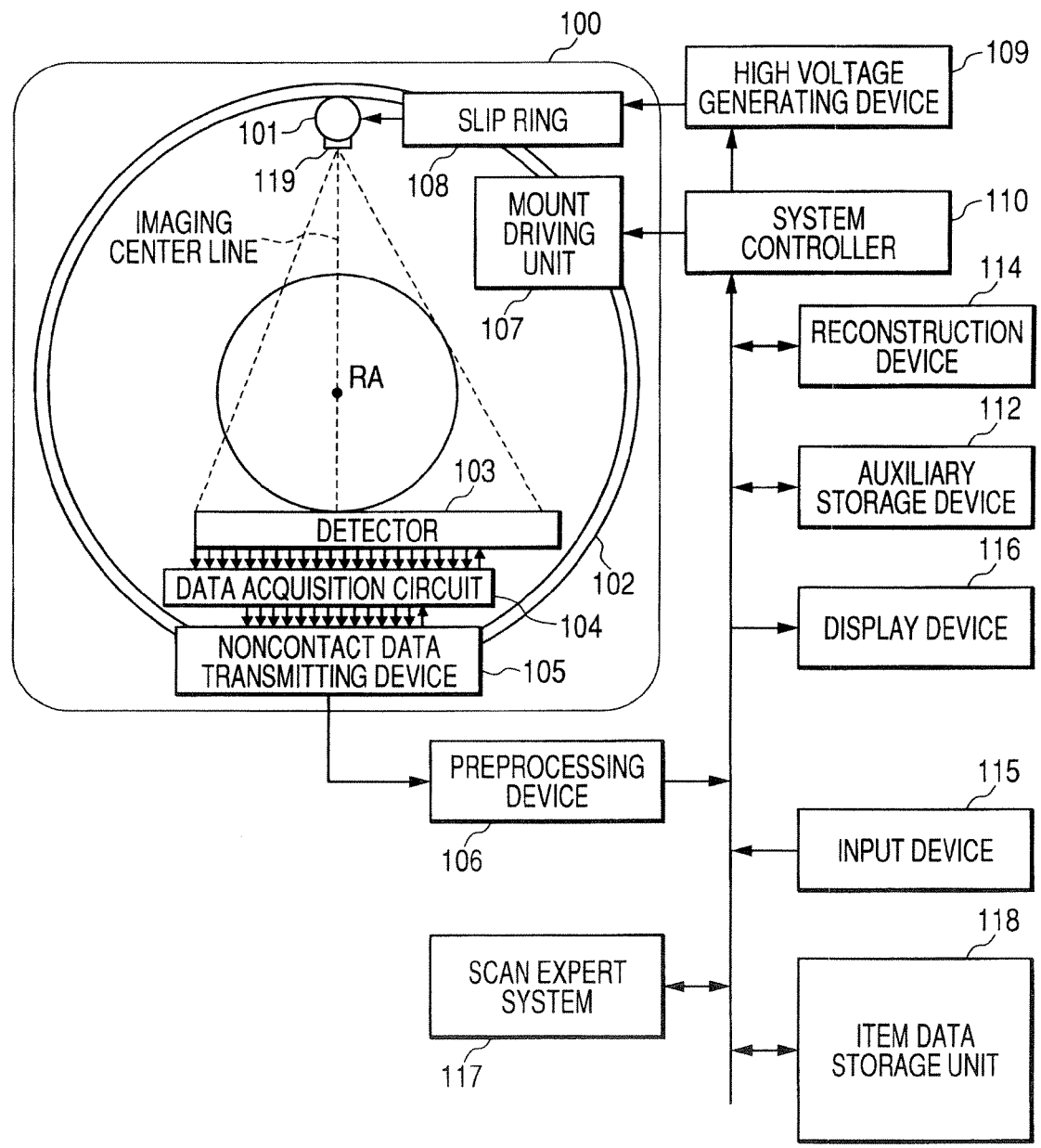
FIG. 1 is diagram showing a configuration of an X-ray computed tomographic apparatus according to an embodiment of this invention.

FIG. 1 shows a configuration of an X-ray computed tomographic apparatus according to an embodiment of this invention. A gantry 100 has an X-ray tube 101 and a multichannel type X-ray detector 103. A collimator 119 that forms an X-ray is connected to the X-ray tube 101. The X-ray tube 101 and the X-ray detector 103 are loaded on a circular frame 102 that is rotatably supported around a rotational axis RA. The X-ray detector 103 faces the X-ray tube 101. During rotation due to being driven by a mount driving unit 107, an X-ray tube voltage is continuously or intermittently applied from a high voltage generating device 109 to the X-ray tube 101 via a slip ring 108. Thereby, the X-ray is continuously or intermittently radiated from the X-ray tube 101. The X-ray detector 103 has a plurality of detecting elements, for example, 916 channels of detecting elements are arranged in a channel direction in order to detect X-rat transmitting an object.

Figure 2:
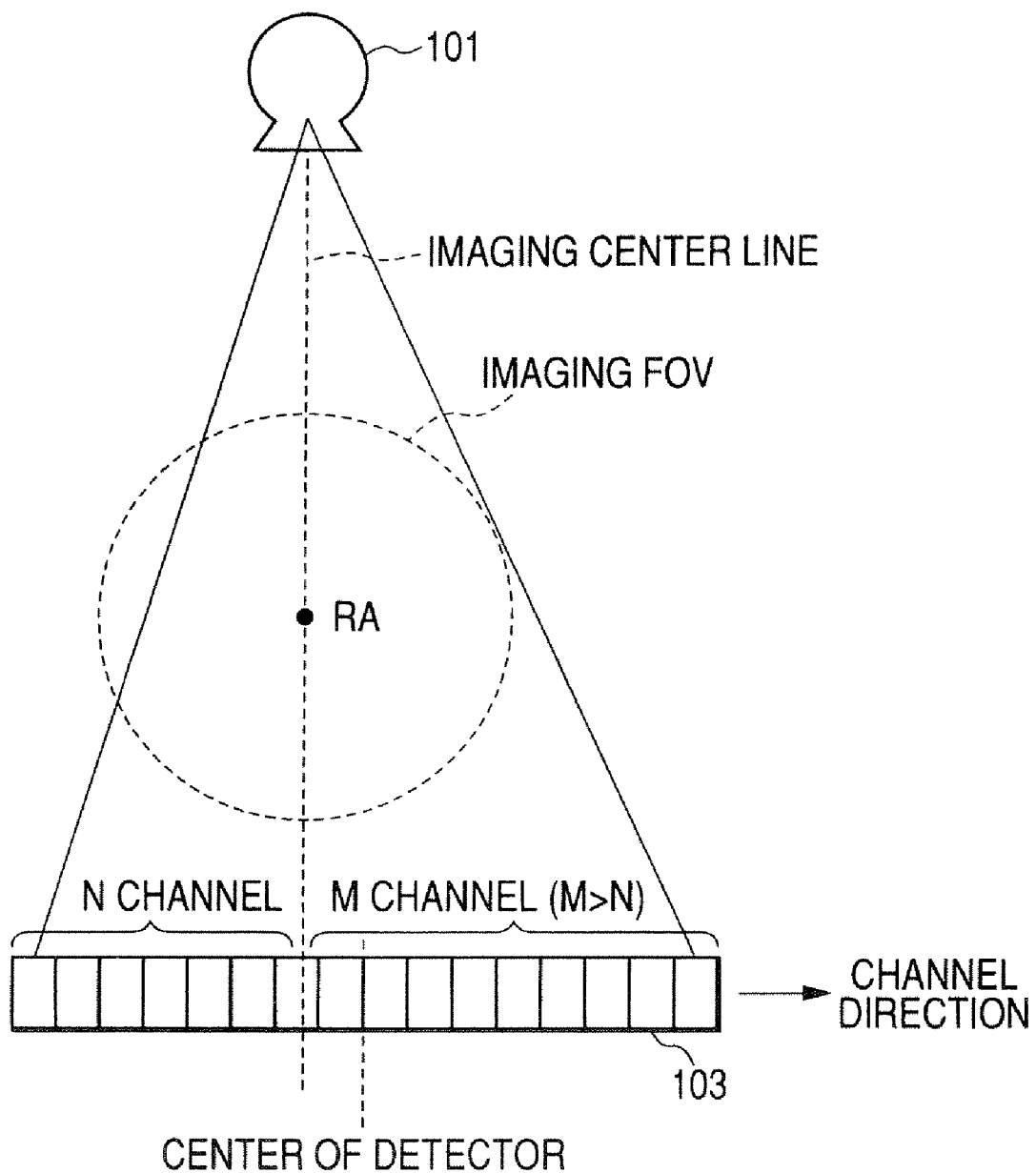
FIG. 2 is a detailed diagram showing an asymmetrical X-ray detector of FIG. 1.

As shown in FIG. 2, the X-ray detector 103 is asymmetrically disposed on the frame 102 in order to magnify a field of view for imaging (imaging FOV). According to this arrangement, a field of view for the scanogram is asymmetric with respect to an imaging center line in a direction perpendicular to a rotational axis. Further, the imaging center line is defined by a line connecting a focal point of the X-ray tube 101 and the rotational axis RA.

The X-ray detector 103 is disposed such that a detection region (sensitivity range) of X-ray that transmits the object is asymmetric with respect to the imaging center line in a channel direction (a direction perpendicular to the rotational axis RA). The center position of the X-ray detector 103 is shifted to one side of the channel direction from the imaging center line. Specifically, a number of channels M at one side of the imaging center line is larger than a number of channels N at the other side, and the sensitivity range at the one side is larger than the sensitivity range at the other side. The detecting elements for detecting an X-ray that transmits the objects are asymmetrically arranged with respect to the imaging center line.

The collimator 119 provided in the X-ray tube 101 asymmetrically forms the X-ray corresponding to the arrangement of the X-ray detector 103. However, the X-ray detector 103 may be symmetrically disposed and only the X-ray may be asymmetrically formed by the collimator 119.

It is not limited to asymmetrically disposing the X-ray detector 103 so as to be fixed to the frame 102. The X-ray detector 103 may be disposed on the frame 102 so as to be moved along the channel direction. In this case, the X-ray detector 103 can be symmetrically or asymmetrically disposed and the proportion of asymmetrical arrangement can be appropriately controlled.

Returning to FIG. 1, a data acquisition circuit 104 (generally referred to as DAS (data acquisition system)) converts a signal output from the detector 103 for every channel into a piezoelectric signal, amplifies, and then converts into a digital signal. Data (raw data) is sent to a preprocessing device 106 that is accommodated in a console disposed outside the gantry via a noncontact data transmitting device 105. A correction process such as a sensitivity correction is performed on the data and then the data is stored in an auxiliary storage device 112 as projection data immediately before reconstruction process.

The auxiliary storage device 112 is connected to a reconstruction device 114, a display device 116, an input device 115, a scan expert system 117 (scan scheduling unit), an item data storage unit 118, and a system controller 110 via a data/control bus.

Specific training is needed to optimize scanning conditions such as an X-ray tube voltage, an X-ray current, an X-ray radiation time, etc. or reconstructing conditions such as a thickness of slice, the number of slices, a size of slice, etc. The scan expert system 117 is developed in order to make it possible for even a person who has a narrow experience or lack specific training to set the conditions on the basis of the specific training. The scan expert system 117 has a specific function for supporting the operation of setting the scano angle of the scanogram (hereinafter, simply referred to as scanogram angle) by using a graphical user interface (GUI) that uses item data previously stored in the item storage unit 118.

The following data is stored in the item data storage unit 118 as item data. The data is as follows:
- picture data that schematically represents the X-ray tube,
- picture data that schematically represents sectorial or triangular X-ray irradiation area,
- picture data that schematically represents a body seen from the head,
- picture data that schematically represents a body seen from the feet,
- data including character information indicating that the body is inserted into the gantry 100 from the head,
- data including character information indicating that the body is inserted into the gantry 100 from the feet,
- data including character information indicating that a portion of the X-ray irradiation region at the left side of the object is wide and a portion at the right side of the object is narrow,
- data including character information indicating that a portion of the X-ray irradiation region at the right side of the object is wide and a portion at the left side of the object is narrow,
- data including character information indicating that a portion of the X-ray irradiation region at the top side (front) of the object is wide and a portion at the bottom side (back) of the object is narrow, and
- data including character information indicating that a portion of the X-ray irradiation region at the bottom side of the object is wide and a portion at the top side of the object is narrow.

The above picture data can be replaced by photograph data.

Figure 3:
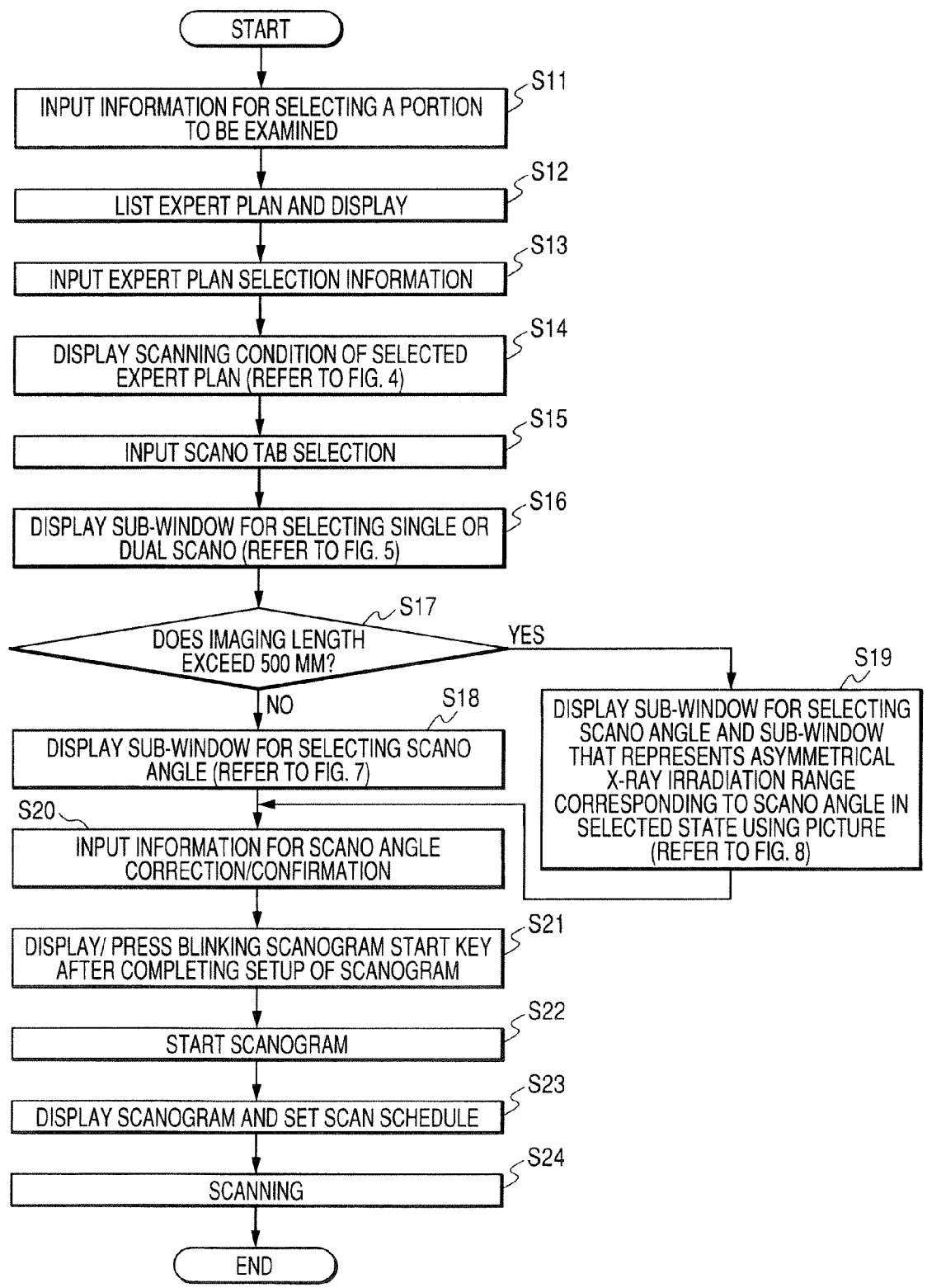
FIG. 3 is a flowchart showing processes from a scanning schedule to scanning completion in a scan expert system of FIG. 1.
Figure 6:
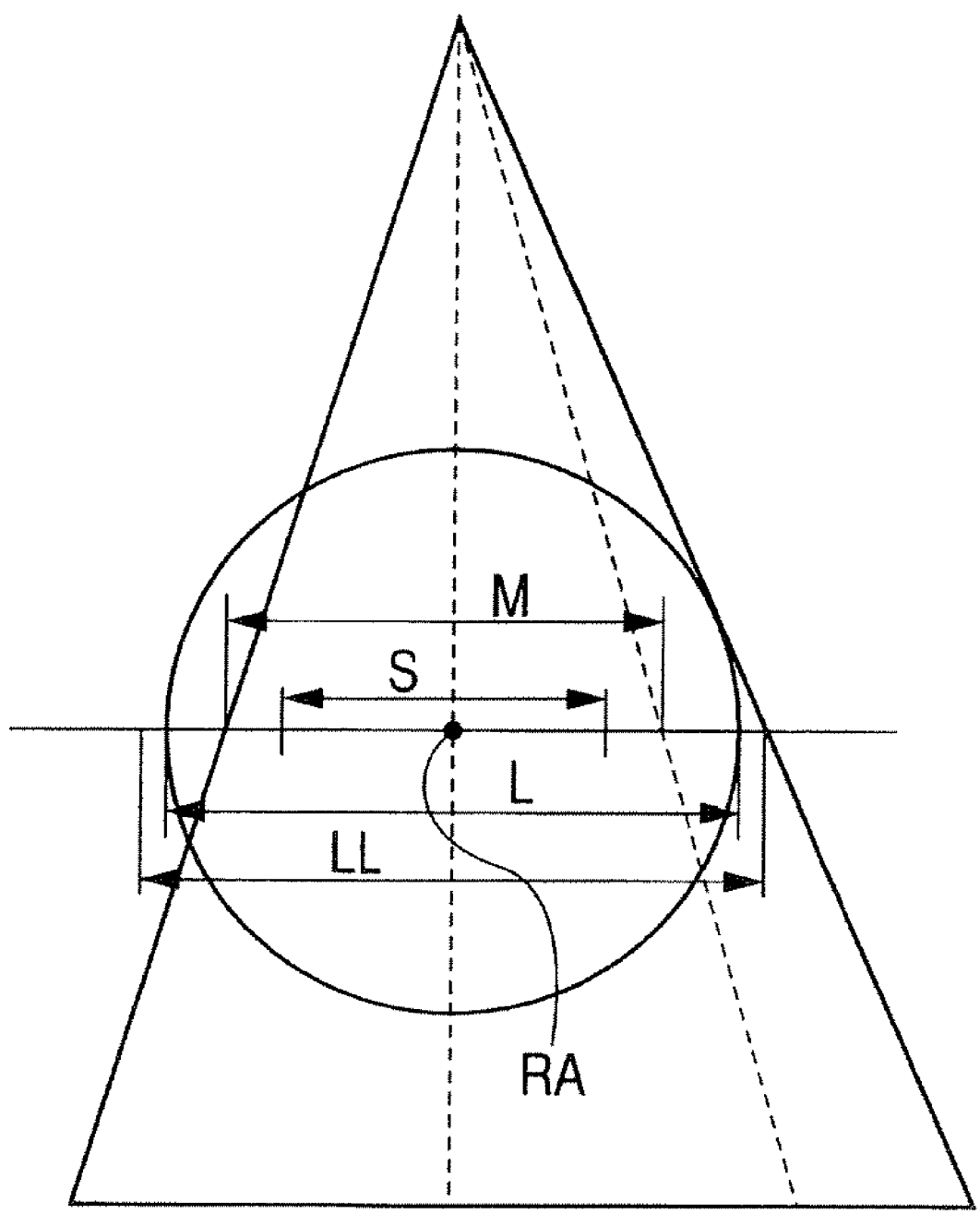
FIG. 6 is a supplementary explanation view of S17 of FIG. 3.

FIG. 3 is a flowchart showing processes from scanning schedule to scanning completion in the scan expert system 117. Information for selecting a portion to be examined is input to the scan expert system 117 through the input device 115 (S11). The scan expert system 117 lists a plurality of expert plans corresponding to various examination objects regarding the selected portion and then display on the display device 116 (S12). The expert plans include from scanogram to scanning schedule suitable for examination portions and objects, a series of operation processes to one or more main scan operations (acquisition of projection data), and setting recommended imaging conditions and scanning conditions. The imaging conditions include a scanogram angle (position of tube), a direction of the object that is inserted into the gantry 100 (the object is inserted from the head or the feet), an X-ray tube voltage, an X-ray tube current, an imaging length, an imaging direction (a moving direction of a top panel), etc. The scanning conditions include a stop scanning period, a start scanning position, a completed scanning position, a scan mode (single/helical), an X-ray tube voltage, an X-ray tube current, a size of imaging FOV, a thickness of the imaging slice. The imaging length refers to a size of the scanogram region, and is defined by a long side of rectangular imaging region on a plane perpendicular to the imaging center line by passing the rotational axis. The imaging length of the channel direction is selected by inputting a numerical value or among standardized sizes (S, M, L, LL) that are previously provided, as shown in FIG. 6. A recommended value is initially set to the respective parameters of the imaging conditions and the scanning conditions.

Figure 4:
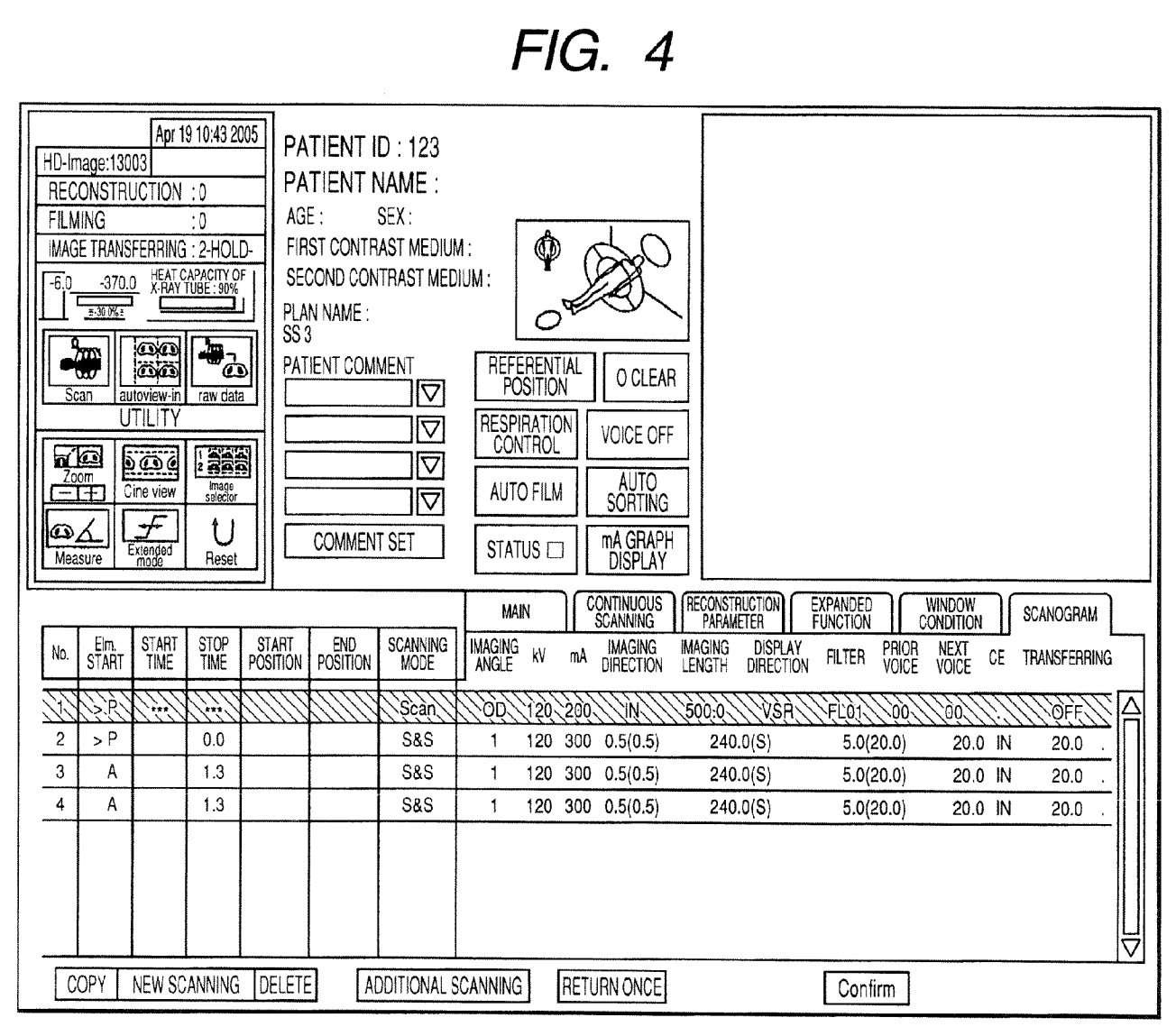

Information for selecting an expert plan is input to the scan expert system 117 through the input device 115 (S13). Image data for displaying the selected expert plan, the imaging conditions, and the scanning conditions is created by the scan expert system 117. The selected expert plan is displayed on the display device 116 on the basis of the image data as shown in FIG. 4 (S14).

Figure 5:
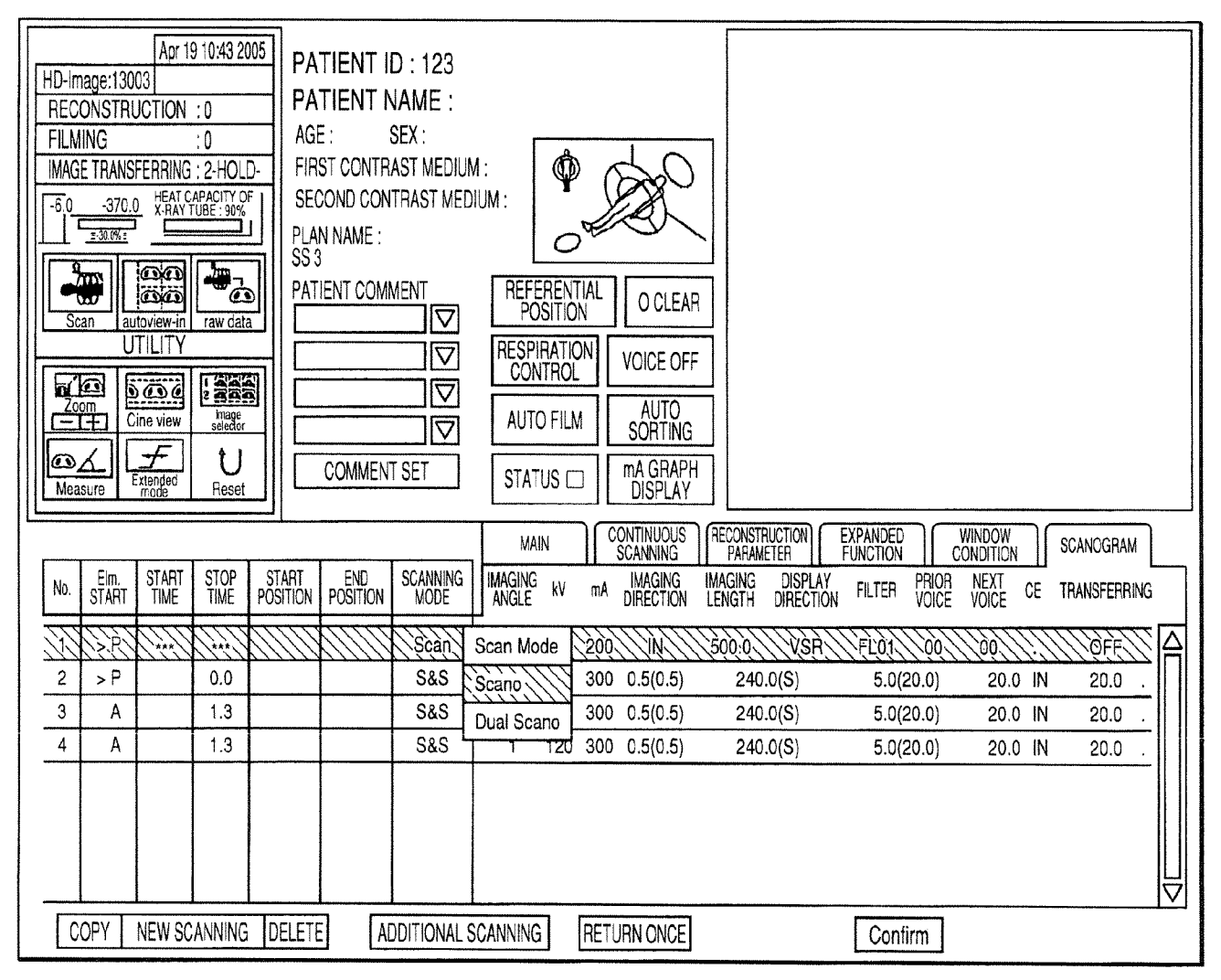

When clicking a scanogram tab on the display screen of the expert plan, the imaging conditions for performing the scanogram are displayed (S15). As shown in FIG. 5, by moving a pointer onto a row of the scanogram and then clicking it, the row of the scanogram becomes a selected state (white to black inverted). In this state, when the pointer is clicked on 'scanogram', a sub-window for selecting a scanogram mode is displayed (S16). For example, the scanogram mode includes a (single) scanogram mode that performs the scanogram in one direction by using only one tube, and a (dual) scanogram mode that simultaneously performs the scanogram in two directions by using two tubes that are shifted from each other by 90°. One of the scanogram modes is selected, and the selection information is input to the scan expert system 117. Further, the other conditions such as the X-ray tube voltage, the X-ray tube current, the imaging length, the imaging direction can be appropriately corrected as necessary.

Next, the scan expert system 117 compares a set imaging length with a predetermined length (S17). The predetermined length is determined by the maximum range that is capable of equally imaging the right and left sides of the scanogram by the asymmetrical X-ray detector 103. As shown in FIG. 6, it is possible to equally image at the right and left sides with the standardized sizes S, and M. However, an asymmetrical imaging is performed at the right and left sides with the sizes L, LL that are larger than the sizes S, and M. As the predetermined length that is compared with the set imaging length, the size M or a length corresponding to the size M is previously set to 500 mm.

Figure 7:
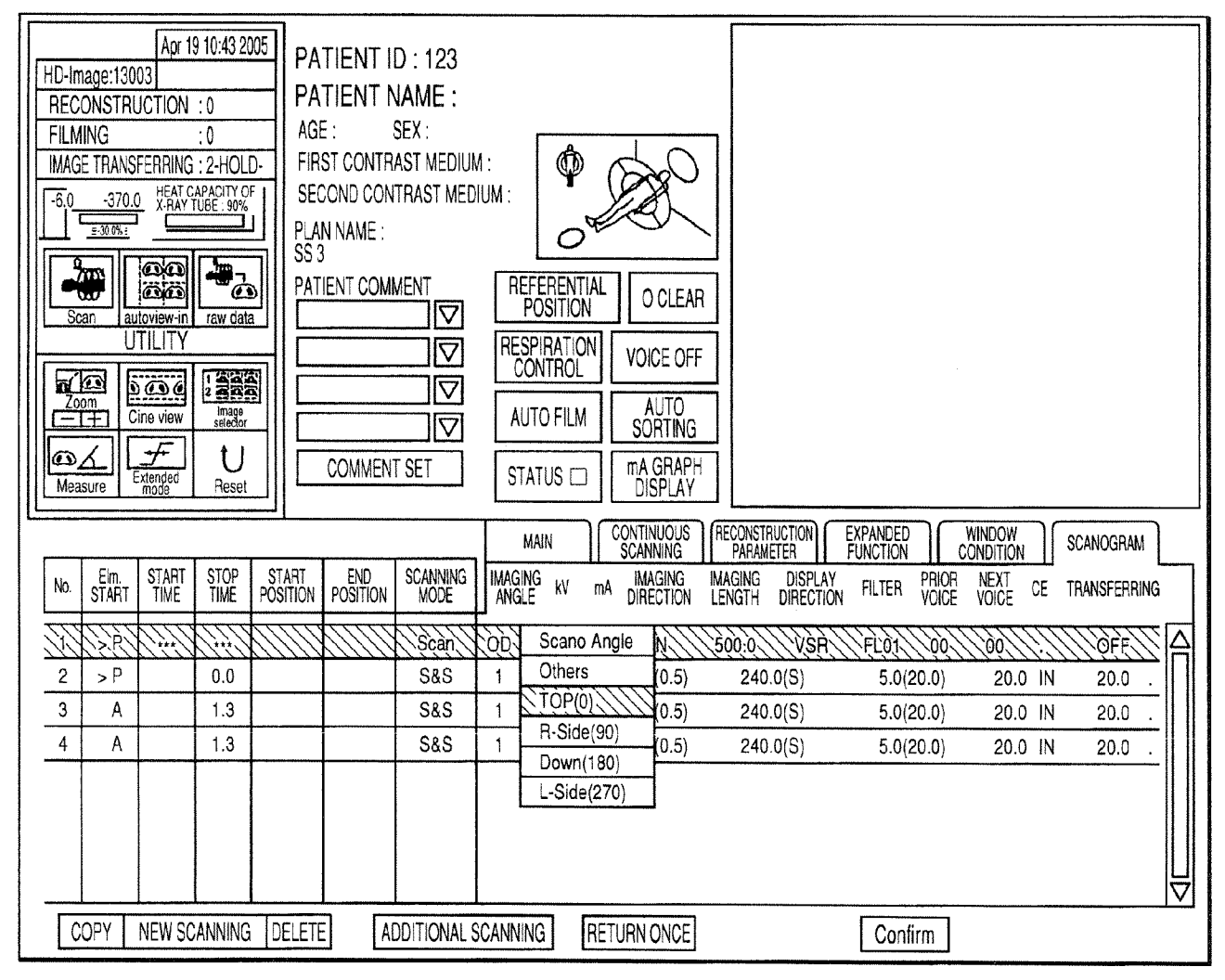

When the set imaging length does not exceed 500 mm, a sub-window for selecting a scanogram angle is displayed by the scan expert system 117, as shown in FIG. 7 (S18). TOP (0) indicates that the X-ray tube 101 is positioned at the top (0°) of a rotating line, and the object is imaged from the front. R-side (90) indicates that when the X-ray tube 101 rotates by 90° from the top of the rotating line, the object is imaged from the right side thereof. DOWN (180) indicates that the X-ray tube 101 is positioned at the bottom (180°) of the rotating line and the object is imaged from the back thereof. L-side (270°) indicates that when the X-ray tube 101 rotates by 270° from the top of the rotating line, the object is imaged from the left side thereof. The display type of the scanogram angle that is in a present selection state is different from the type of another scanogram angle. The other scanogram angle is connected as necessary (S20).

Figure 8:
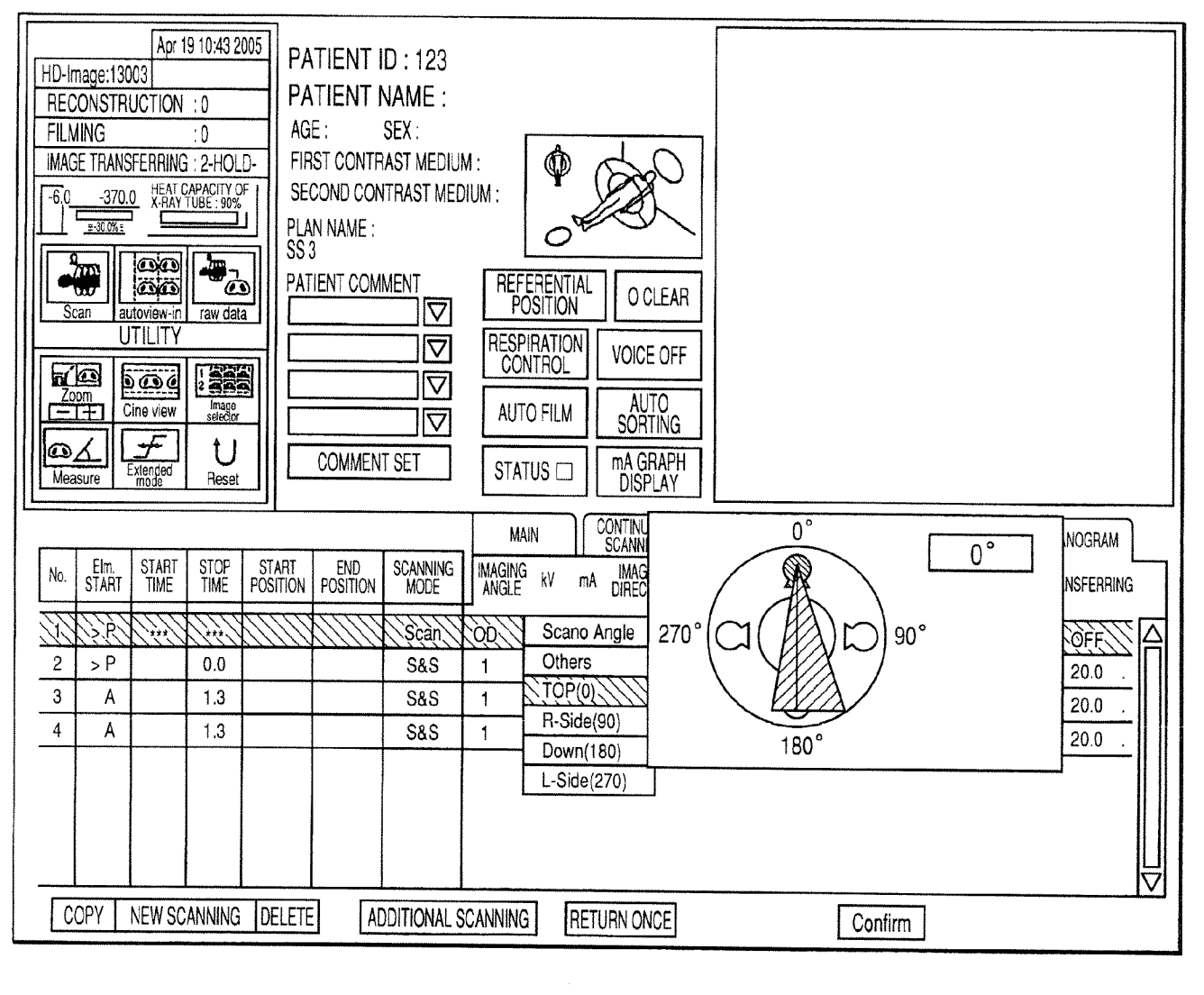
Figure 9:
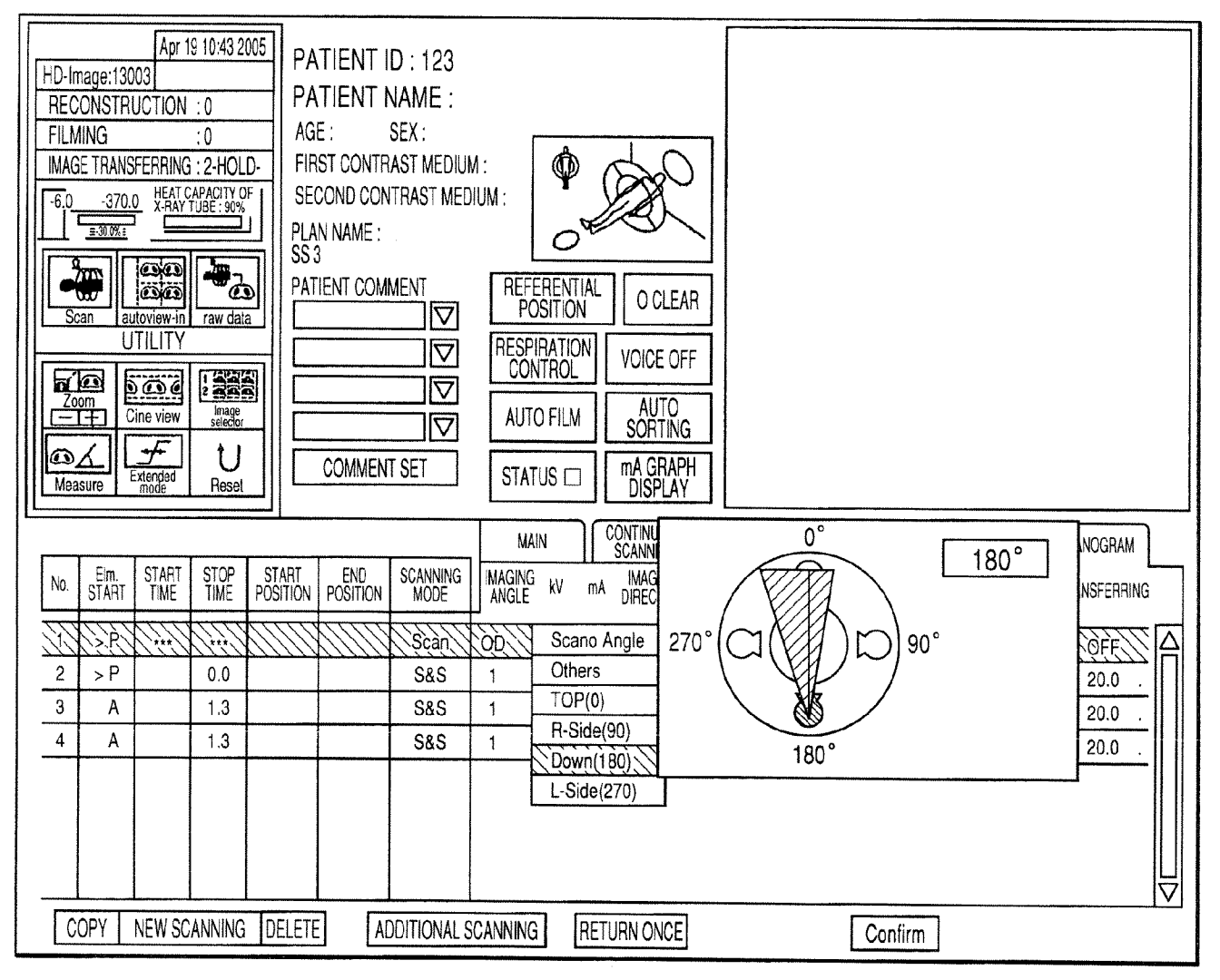

Meanwhile, when the set imaging length exceeds 500 mm, the scan expert system 117 creates the sub-window for selecting the scanogram angle and another sub-window (a sub-window for confirming the scanogram angle) that displays the asymmetrical X-ray irradiation region corresponding to the scanogram angle shown in FIGS. 8 and 9 as a schematic picture and displays both sub-windows (S19).

Figure 10A:
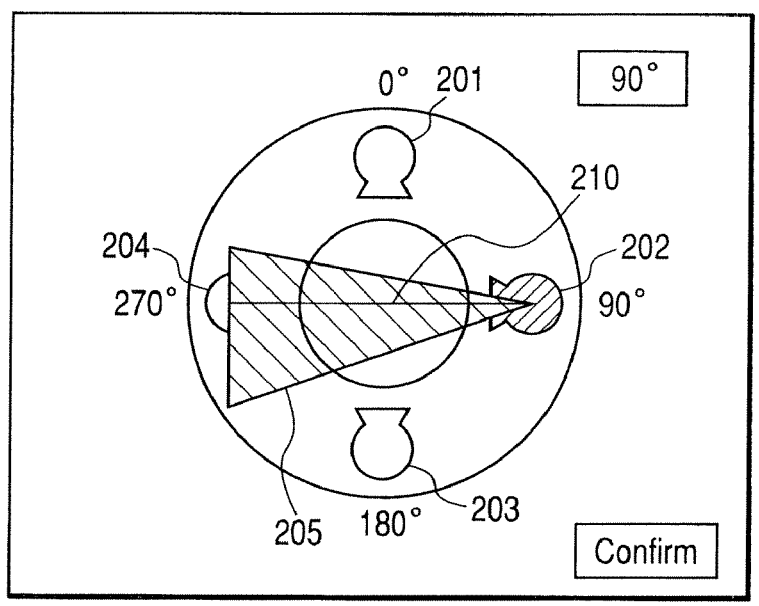
FIG. 10A is a diagram showing another example of a sub-window of FIGS. 8 and 9.

As shown in FIG. 10A in detail, an X-ray mark 205 that represents the asymmetrical X-ray irradiation region by using a sectorial or triangular picture corresponds to the scanogram angle that is in a selected state. An imaging center line 210 is positioned on the X-ray mark 205. The imaging center line 210 connects a focal point of the X-ray and the rotational axis RA. In addition to the X-ray mark 205, icons 201, 202, 203, and 204 that represent X-ray tubes corresponding to positions of 0°, 90°, 180°, and 270° by using pictures are arranged. A display shape of a selected icon (202 in FIG. 10A) is different from that of non-selected icons (201, 203, and 204 in FIG. 10A). For example, the selected icon is displayed by a black pattern, but the non-selected icons are displayed by a white pattern. In addition to the X-ray mark 205, and the X-ray icons 201, 202, 203, and 204, scanogram angle is represented by using characters. For example, in FIG. 10A, 90° is displayed as characters. As necessary, when one of the non-selected icons 201, 203, and 204 is clicked and then "confirm" is clicked, the displayed scanogram angle is changed into the clicked scanogram angle (S20).

Figure 10B:
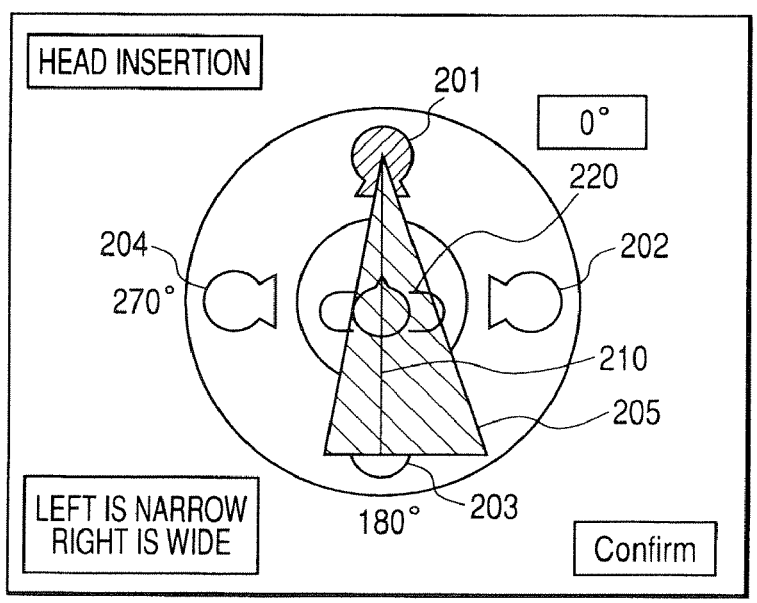
FIG. 10B is a diagram showing another example of a sub-window of FIGS. 8 and 9.
Figure 10C:
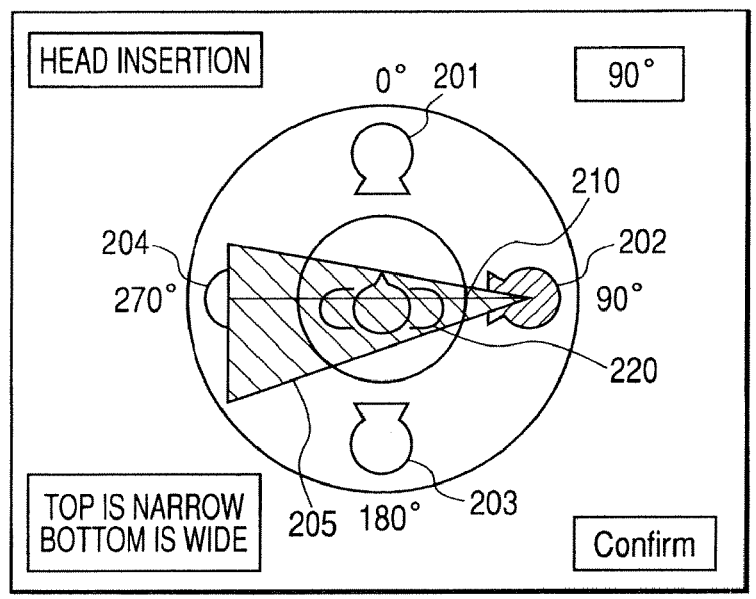
FIG. 10C is a diagram showing another example of a sub-window of FIGS. 8 and 9.
Figure 10D:
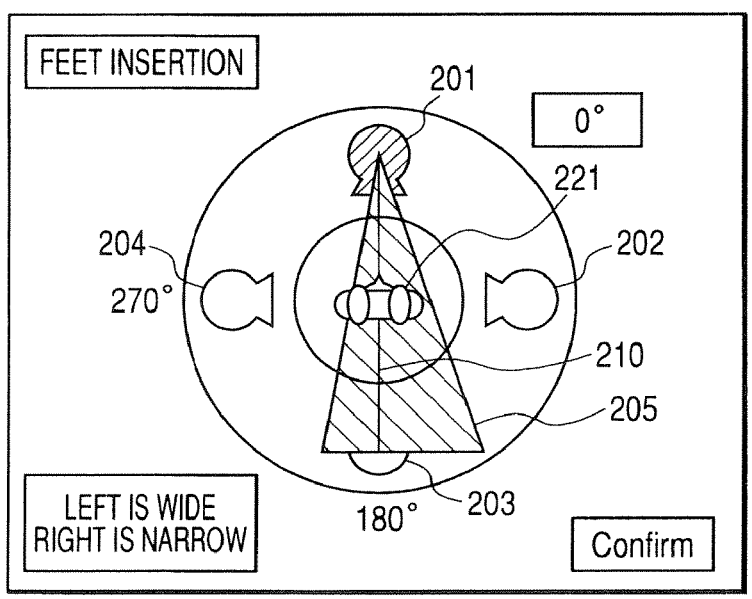
FIG. 10D is a diagram showing another example of a sub-window of FIGS. 8 and 9.
Figure 10E:
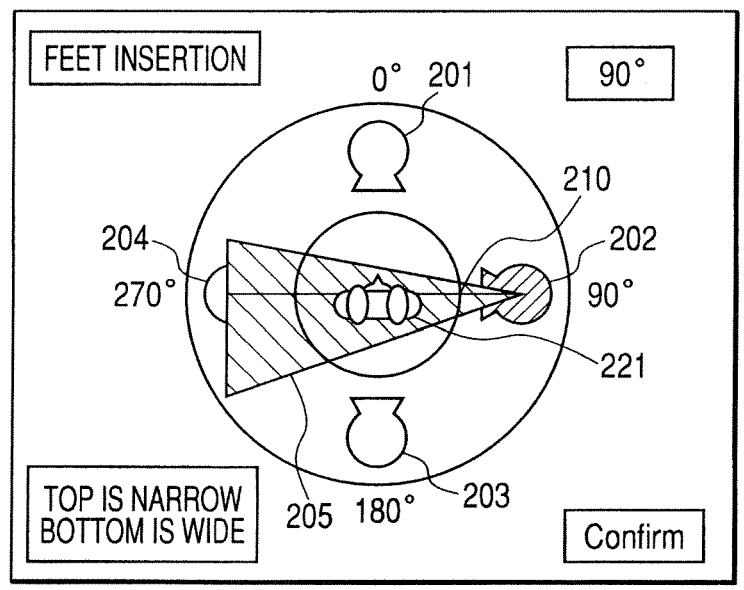
FIG. 10E is a diagram showing another example of a sub-window of FIGS. 8 and 9.

Further, in the sub-window of FIG. 10A, a body mark 220 that represents a state when the object is inserted into the gantry 100 from the head using a picture as shown in FIGS. 10B and 10C or another body mark 221 that represents a state when the object is inserted into the gantry 100 from the feet using a picture as shown in FIGS, 10D and 10E may be disposed around the imaging center line. The selection of the body marks can be determined from the imaging condition. By displaying the body marks 220 and 221, it is possible to easily and visibly understand the relationship between the wide and narrow portion of the X-ray irradiation region and the right and left of the object. In addition to the body marks 220 and 221, it is preferable to provide the state that the object is inserted from the head and the state that the object is inserted from the feet as character information such as "head insertion" or "feet insertion", respectively. Further, the relationship between the wide and narrow portion of the X-ray irradiation region and the right and left of the object may be indicated as character information such as "the left is narrow, and the right is wide", "the top is narrow, and the bottom is wide", "the left is wide and the right is narrow", "the top is narrow and the bottom is wide", etc. In this case, the right or left is determined based on the object.

Figure 11:
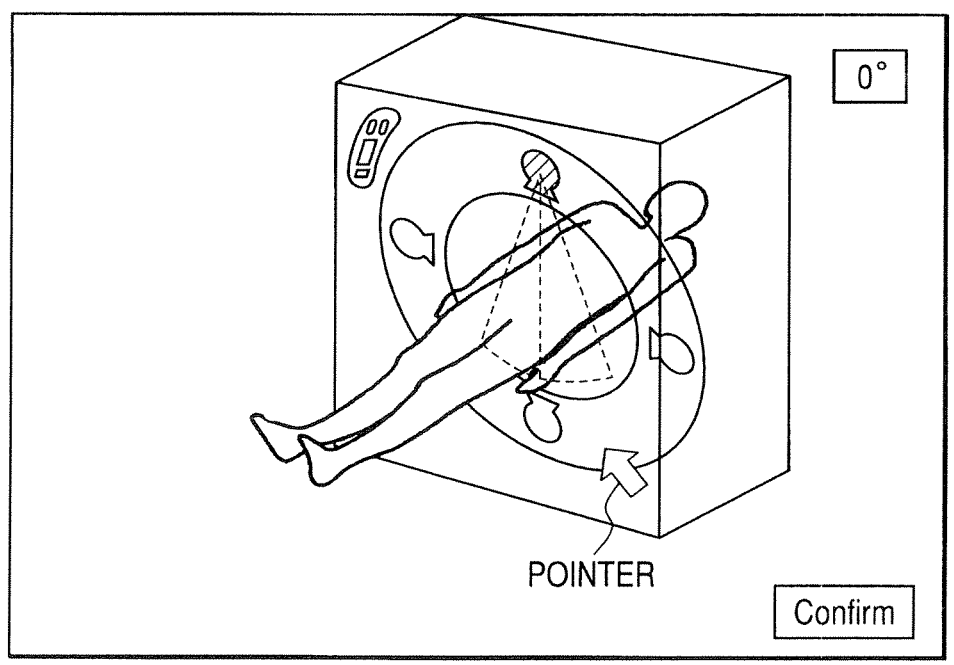
FIG. 11 is a diagram showing another example of a sub-window of FIGS. 8 and 9.

The picture in the sub-window of FIG. 10A may be represented as a three-dimensional picture together with an object mark as shown in FIG. 11. In this case, the scanogram angle may be selected by automatically setting the scanogram angle by indicating an area or a portion with a wide field of view using a pointer in addition to clicking the icons 201, 202, 203, and 204.

Figure 12:
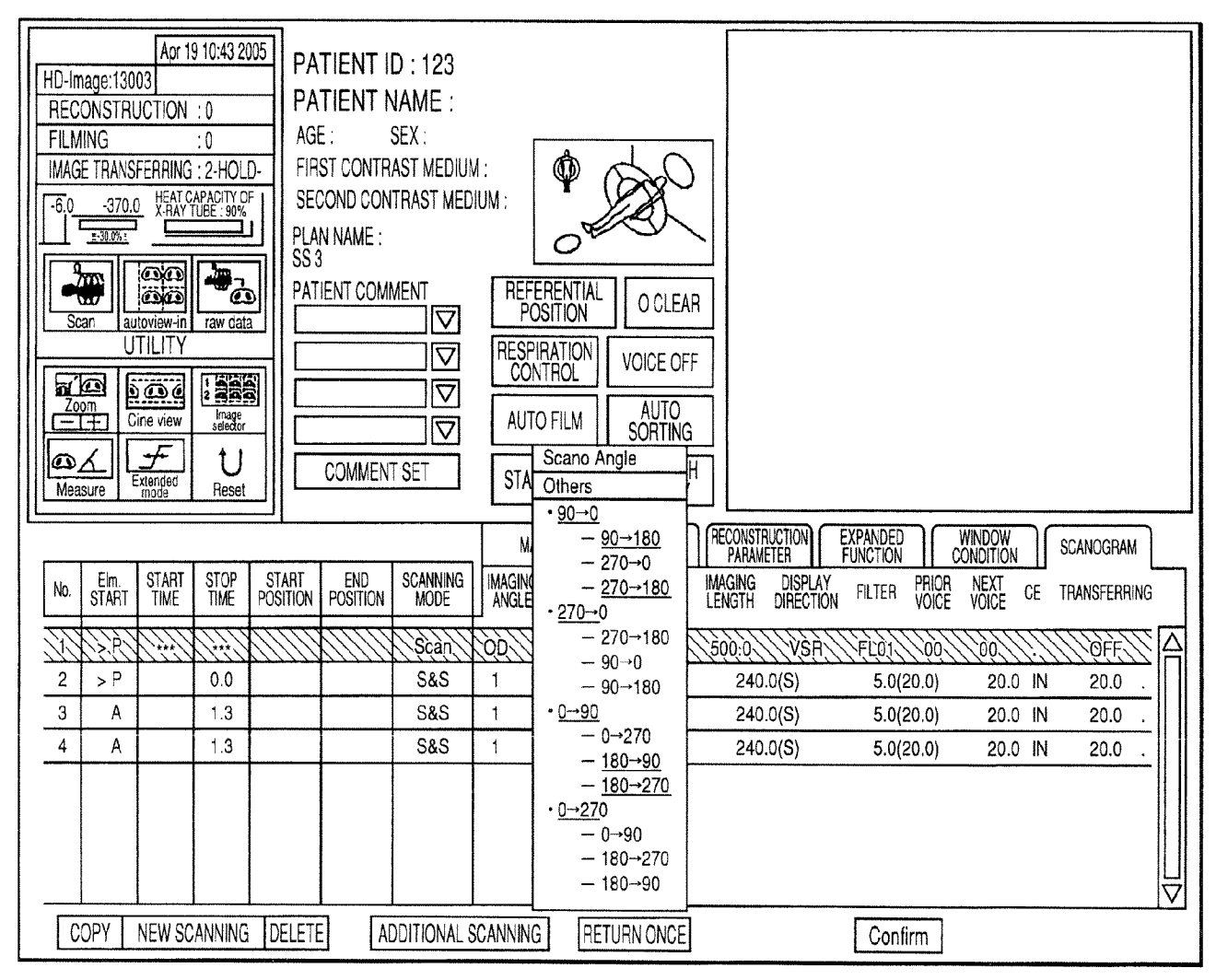
Figure 13:
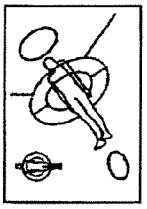
FIG. 13 is a diagram showing an example of a screen display at scanogram angles of 0°/90° corresponding to FIG. 8 in the case of a double tube type X-ray CT apparatus.
Figure 14:
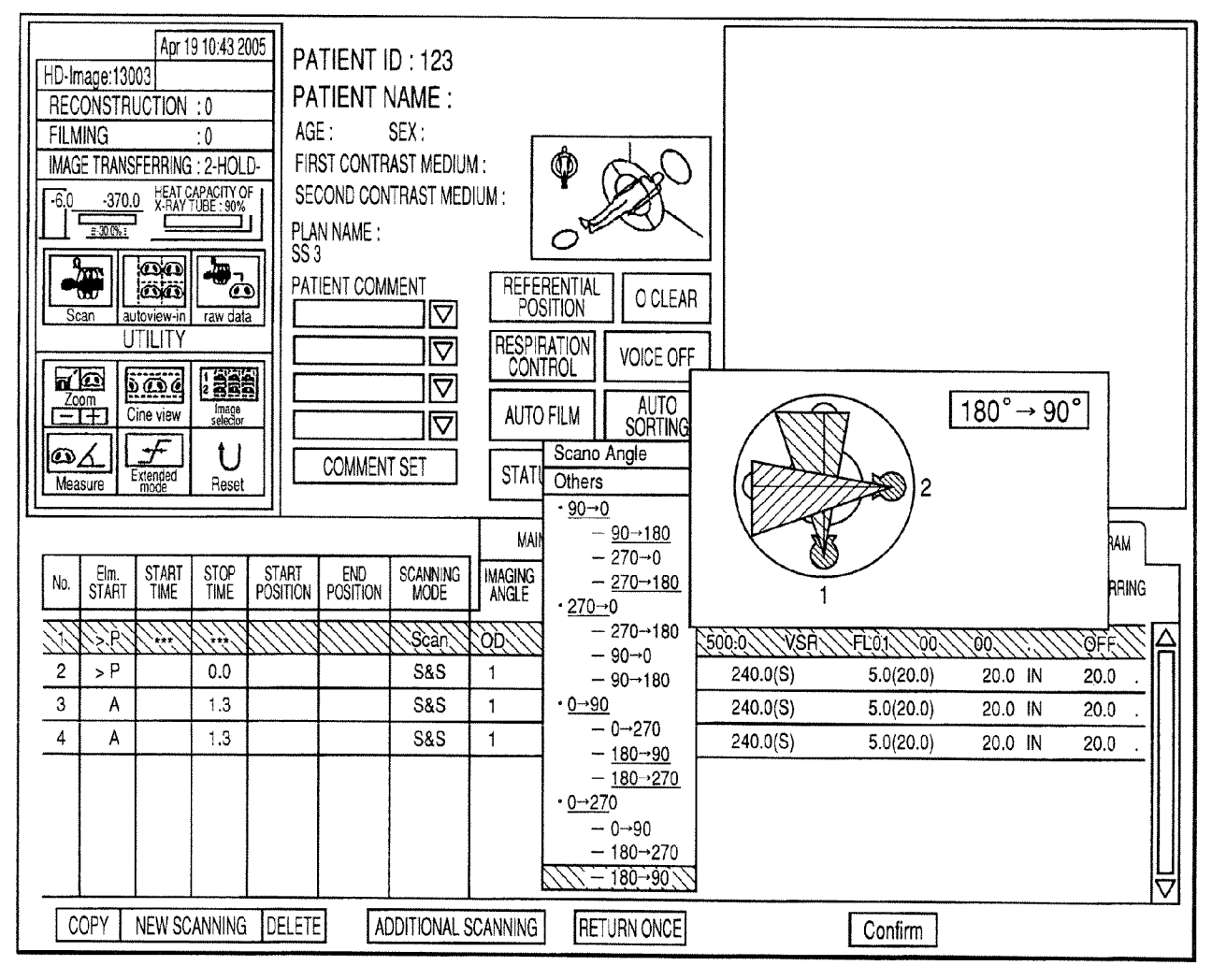
Figure 15:
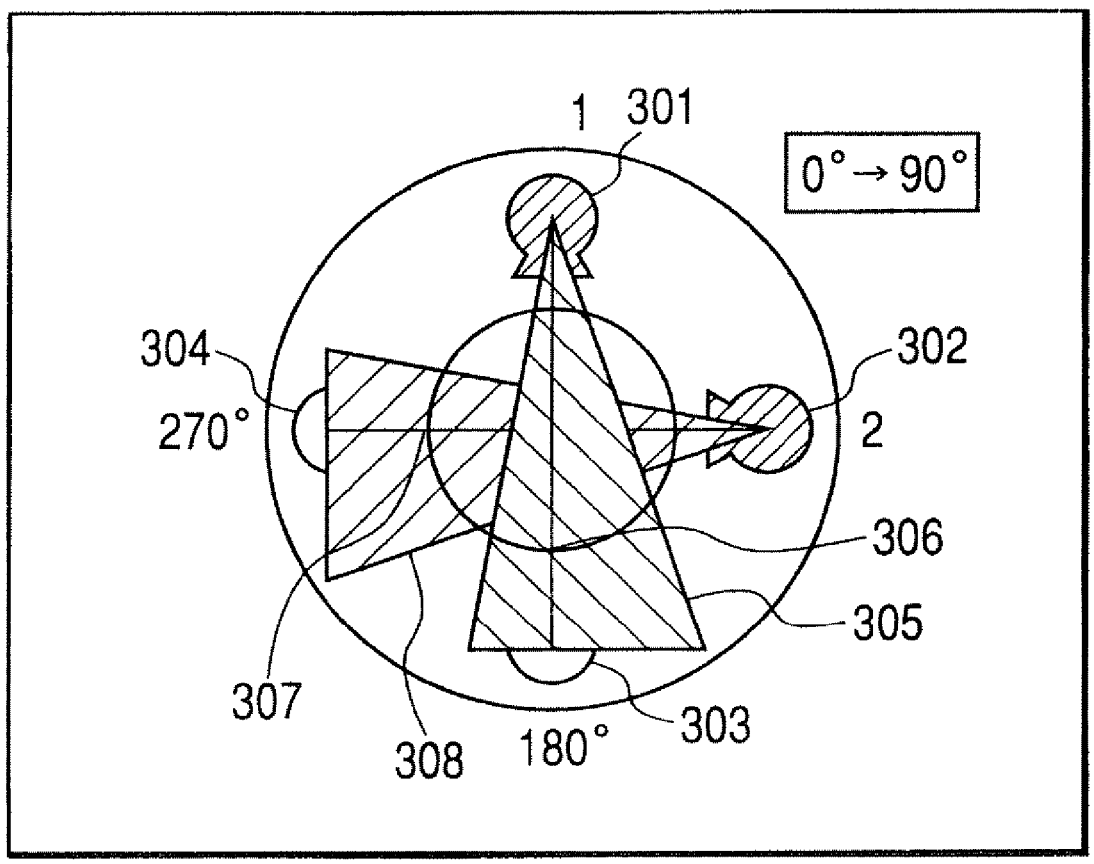
FIG. 15 is a diagram showing a sub-window corresponding to a scanogram angle of FIG. 13.

In the step S16 (see FIG. 5), when selecting a (dual) scanogram that images the scanogram in two directions at the same time using two tubes, as shown in FIG. 12, a sub-window for selecting a two directional scanogram angle is displayed. A main scanogram is imaged in one of the two directions, and a sub-scanogram is imaged in the other direction. On a sub-window, selection bars are listed as "(a scano angle of the main scanogram) ->(a scano angle of the sub-scanogram)". When a scano angle of main/sub scanogram is selected, as shown in FIGS. 13 and 14, a sub-window that represents the selected scanogram angles of the two asymmetrical X-ray irradiation regions using schematical pictures is created. As shown in FIG. 15 in detail, an X-ray mark 305 indicating an X-ray irradiation region asymmetric with respect to the imaging center line 306 corresponding to the main scanogram is arranged correspondingly to an angle of the main scanogram. Similarly, an X-ray mark 307 indicating an X-ray irradiation region asymmetric with respect to the imaging center line 308 corresponding to the sub scanogram is arranged correspondingly to an angle of the sub scanogram. In addition to the X-ray marks 305 and 307, icons 301, 302, 303, and 304 that resemble the X-ray tube are disposed on positions corresponding to 0°, 90°, 180°, and 270°. The display types of the icons 301 and 302 that are in selected positions are different from those of the icons 303 and 304 that are in non-selected states. As necessary, when the non-selected icons 303 and 304 are clicked and then "confirm" is clicked, the displayed scanogram angle is changed into the clicked scanogram angle.

The completion of setting the scanogram conditions including the scanogram angle is done by clicking the "confirm" button. The setting of the scanogram is started by controlling the system controller 110 according to the scanogram conditions by clicking the "confirm" button. In detail, the X-ray tube 101 moves into a set scanogram angle position, and then preparation operations such as heating a cathode filament of the X-ray tube 101, raising a voltage of the high voltage generating device 109, etc. are started.

After completing the setup, a scanogram start key that blinks on the input device 115 is pressed (S21) by a user to start the scanogram which responds to the control of the system controller 110 (S22). Imaged scanogram data is sent to the scan expert system 117 from the auxiliary storage device 112. The scan expert system 117 creates image data for a scan scheduling screen including a scanogram. The scan schedule screen is displayed on the display device 116 on the basis of the image data. On the scanning schedule screen, detailed conditions including a scanning region are set, and confirmed (S23). The scanning is performed by controlling the system controller 110 on the basis of the scanning condition (S24).

Figure 16:
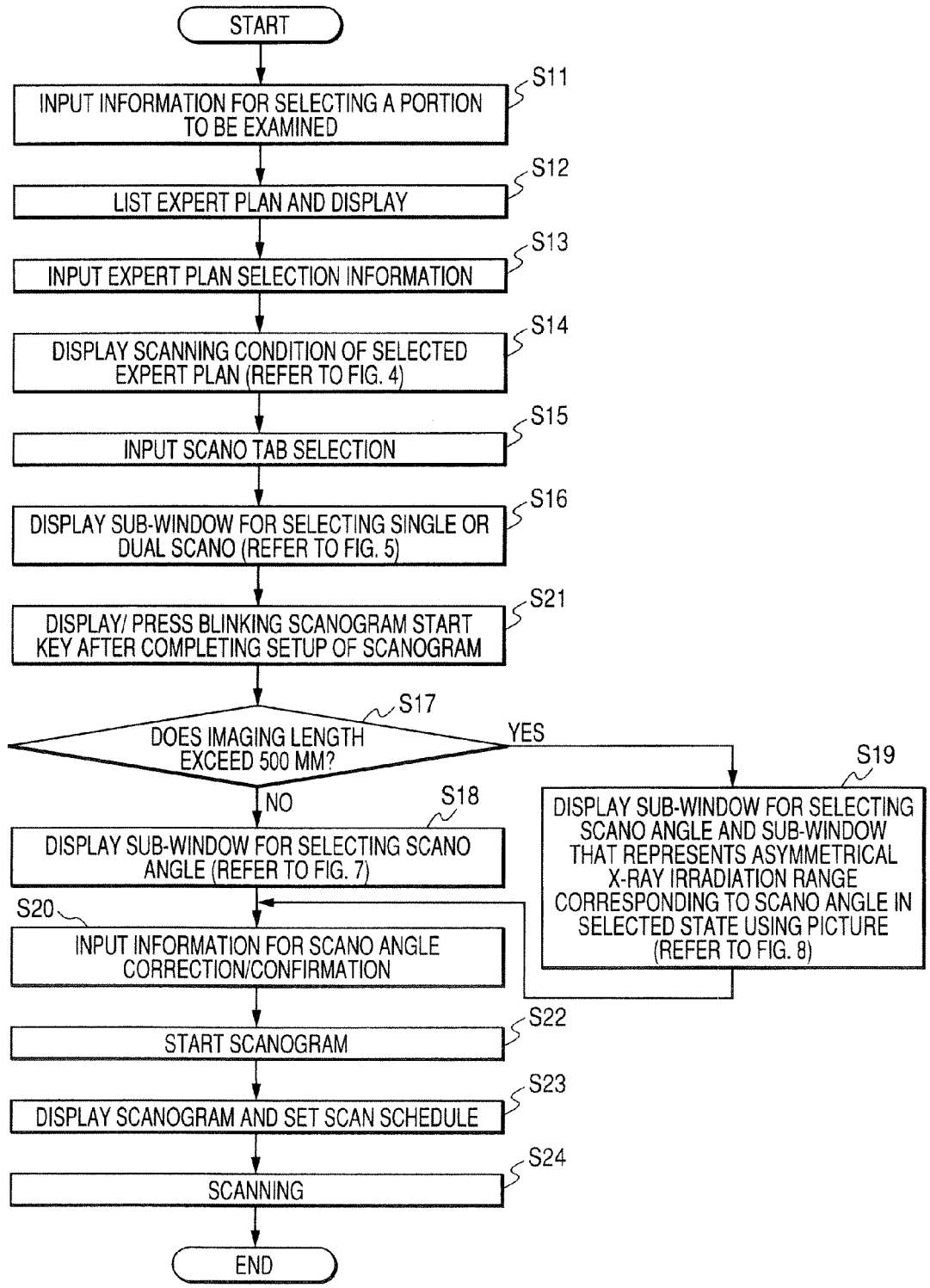
FIG. 16 is a flowchart showing processes of displaying scanogram angle sub-window at the time of pressing a scanogram start key.

Further, in the above description, the sub-window for confirming the scanogram angle (in the step S19) is displayed prior to displaying the blinking scanogram start key after setting the scanogram. However, as shown in FIG. 16, it is further preferable to display the sub-window for confirming the scanogram angle at the time when the blinking scanogram start key is displayed and then a user presses the key.

Therefore, since the asymmetrical X-ray irradiation region is represented by using a schematic picture corresponding to the selected scanogram angle, it is possible to easily differentiate the wide portion and the narrow portion of the X-ray irradiation range and to perceive the scanogram range, thereby improving the operability for setting. Further, by displaying the X-ray irradiation range as a schematic picture and the X-ray tube marks as icons to designate an arbitrary icon, the scanogram can be set. Therefore, it is possible to improve the operability for setting.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray computed tomographic apparatus comprising:
    an X-ray tube that generates X-rays;
    an X-ray detector that detects an X-ray passing through an object;
    a supporting member that rotatably supports the X-ray tube and the X-ray detector around a rotational axis;

a reconstructing unit configured to reconstruct an image on the basis of an output of the X-ray detector;

an information creating unit configured to create information concerning an arrangement of an asymmetrical field of view of the object when a field of view of a scanogram by the X-ray tube and the X-ray detector is asymmetric with respect to an imaging center line in a direction perpendicular to the rotational axis; and a display unit that displays information concerning the arrangement, wherein the information creating unit is configured to create information for displaying an asymmetric sectorial picture that corresponds to the asymmetrical field of view so as to correspond to a scanogram angle, and wherein the information creating unit is configured to create information for displaying a plurality of icons that resemble the X-ray tube, and correspond to scanogram angles together with the asymmetrical sectorial picture.

2. The X-ray computed tomographic apparatus according to claim 1, wherein when any one of the plurality of icons is selected, the direction of the asymmetric sectorial picture is changed.

3. The X-ray computed tomographic apparatus according to claim 1, wherein the information creating unit creates information for displaying a body mark indicating the object together with the asymmetric sectorial picture.

4. The X-ray computed tomographic apparatus according to claim 1, wherein the information creating unit creates information for displaying a body mark as seen from a body or feet of the object together with the asymmetrical sectorial picture.

5. The X-ray computed tomographic apparatus according to claim 1, wherein the values of the scanogram angles are 0°, 90°, 180°, and 270°.

* * * * *